United States Patent
Johnson et al.

(10) Patent No.: US 9,827,260 B2
(45) Date of Patent: Nov. 28, 2017

(54) COMPOSITION FOR BUFFERED AMINOALKYL GLUCOSAMINIDE PHOSPHATE COMPOUNDS AND ITS USE FOR ENHANCING AN IMMUNE RESPONSE

(71) Applicant: GlaxoSmithKline Biologicals s.a., Rixensart (BE)

(72) Inventors: David Johnson, Research Triangle Park, NC (US); David Burkhart, Research Triangle Park, NC (US); Nupur Dutta, Research Triangle Park, NC (US)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 126 days.

(21) Appl. No.: 14/777,091

(22) PCT Filed: Mar. 13, 2014

(86) PCT No.: PCT/IB2014/059731
§ 371 (c)(1),
(2) Date: Sep. 15, 2015

(87) PCT Pub. No.: WO2014/141127
PCT Pub. Date: Sep. 18, 2014

(65) Prior Publication Data
US 2016/0022719 A1    Jan. 28, 2016

Related U.S. Application Data

(60) Provisional application No. 61/791,165, filed on Mar. 15, 2013.

(51) Int. Cl.
*A61K 9/14* (2006.01)
*A61K 31/70* (2006.01)
(Continued)

(52) U.S. Cl.
CPC ........ *A61K 31/7032* (2013.01); *A61K 9/0043* (2013.01); *A61K 9/1617* (2013.01);
(Continued)

(58) Field of Classification Search
None
See application file for complete search history.

(56) References Cited

U.S. PATENT DOCUMENTS 6,525,028 B1    2/2003  Johnson et al.
6,911,434 B2    6/2005  Baldridge et al.
(Continued)

FOREIGN PATENT DOCUMENTS

WO    2001/090129 A2    11/2001
WO    2002/012258 A1    2/2002
(Continued)

OTHER PUBLICATIONS

HW Fung et al., "Optimizing manufacturing and composition of a TLR4 nanosuspension: physicochemical stability and vaccine adjuvant activity" Journal of Nanobiotechnology, Dec. 21, 2013, vol. 21, No. 11, pp. 43.

*Primary Examiner* — Jeffrey T Palenik
(74) *Attorney, Agent, or Firm* — Virginia G. Campen

(57) ABSTRACT

There is provided a composition comprising an aminoalkyl glucosaminide phosphate compound or a pharmaceutically salt thereof and a buffer for use as an immunomodulator.

48 Claims, 9 Drawing Sheets

(51) Int. Cl.

| | |
|---|---|
| *C08B 37/00* | (2006.01) |
| *A61K 31/7032* | (2006.01) |
| *A61K 31/7008* | (2006.01) |
| *A61K 9/00* | (2006.01) |
| *A61K 9/16* | (2006.01) |
| *A61K 39/39* | (2006.01) |
| *A61K 39/00* | (2006.01) |

(52) U.S. Cl.
 CPC .......... *A61K 31/7008* (2013.01); *A61K 39/39* (2013.01); *A61K 2039/55511* (2013.01)

(56) References Cited

U.S. PATENT DOCUMENTS

| | | |
|---|---|---|
| 2002/0048588 A1 | 4/2002 | Johnson et al. |
| 2002/0077304 A1* | 6/2002 | Persing .............. A61K 31/7024 514/42 |
| 2004/0156863 A1 | 8/2004 | Page et al. |
| 2011/0180430 A1* | 7/2011 | Rappuoli ............. A61K 39/145 206/223 |

FOREIGN PATENT DOCUMENTS

| | | |
|---|---|---|
| WO | 2002/048588 A1 | 6/2002 |
| WO | 03/005952 | 1/2003 |
| WO | 2004/005308 A2 | 1/2004 |
| WO | 2004/062599 A2 | 7/2004 |
| WO | 2006/012425 A2 | 2/2006 |
| WO | 2006/016997 A2 | 2/2006 |
| WO | 2006/052820 | 5/2006 |
| WO | 2006/110344 | 10/2006 |
| WO | 2007/085962 | 8/2007 |

* cited by examiner

CRX-601        3-O-acyl-CRX-601 Degradant

CRX-527

CRX-527 degradant
(3-O-deacyl CRX-527, MW=1107.44)

COMPOSITION FOR BUFFERED AMINOALKYL GLUCOSAMINIDE PHOSPHATE COMPOUNDS AND ITS USE FOR ENHANCING AN IMMUNE RESPONSE

CROSS-REFERENCE TO RELATED APPLICATIONS

This application is filed pursuant to 35 U.S.C. §371 as a United States National Phase Application of International Application No. PCT/IB2014/059731 A1 filed Mar. 13, 2014 which claims priority from U.S. Provisional Application No. 61/791,165 filed Mar. 15, 2013.

STATEMENT REGARDING FEDERALLY SPONSORED RESEARCH

Aspects of this invention were made with United States government support pursuant to NIH Contract# HHSN272200900008C, the United States government may have certain rights in the invention.

FIELD OF THE INVENTION

The present invention relates to a composition comprising aminoalkyl glucosaminide phosphate compounds (AGPs) and the use of the composition in or as a vaccine adjuvant or in prophylactic or therapeutic treatments. Methods for using the compositions are also disclosed.

BACKGROUND OF THE INVENTION

Aminoalkyl glucosaminide phosphates (AGPs) are synthetic ligands of the Toll-like Receptor 4 (TLR4). AGPs and their immunomodulating effects via TLR4 are disclosed in patent publications such as WO 2006/016997, WO 2001/090129, and/or U.S. Pat. No. 6,113,918 and have been reported in the literature. Additional AGP derivatives are disclosed in U.S. Pat. No. 7,129,219, U.S. Pat. No. 6,525,028 and U.S. Pat. No. 6,911,434. Certain AGPs act as agonists of TLR4, while others are recognized as TLR4 antagonists. AGPs are known to be useful as vaccine adjuvants and immunomodulators for stimulating cytokine production, activating macrophages, promoting innate immune response, and augmenting antibody production in immunized animals. Previously, AGPs as adjuvants and/or immunomodulators have principally been utilized in the form of an oil-in-water emulsion, typically using sterilized water and glycerol (approximately 2%). There is an on-going need to identify buffers that may be employed with these AGPs in pharmaceutical and/or adjuvant compositions.

SUMMARY OF THE INVENTION

Accordingly, the present invention provides a pharmaceutical composition comprising one or more AGPs and a buffer. The pharmaceutical composition disclosed in the present invention herein may result in one or more of the following benefits: maximum or increased or improved stability of the AGP in a buffered solution and/or maximum or increased or improved potency of the AGP in a buffered solution relative to other AGP aqueous formulations.

Also provided is a buffered AGP composition with improved stability and/or potency at about pH 7 or at a physiologically normal pH, or at a pharmaceutically acceptable pH.

There is also provided a method of treating a subject (or patient such as a human or other mammal) with the composition of the invention.

In accordance with the invention there is provided a composition comprising (i) an aminoalkyl glucosaminide phosphate or a pharmaceutically acceptable salt thereof, and (ii) a buffer. The buffered solution and AGP compound are combined to form a composition having utility as an immunomodulator.

There is further provided a method for modulating the immune response of a subject, preferably a human, comprising administering to said subject an effective amount of the pharmaceutical composition.

Also provided is a method for ameliorating or substantially preventing an infectious disease, an autoimmune disease, a neurologic disease or an allergic or inflammatory condition in a subject, preferably a human, comprising administering to said subject an effective amount of the pharmaceutical composition.

DETAILED DESCRIPTION OF THE INVENTION

Figure 1:
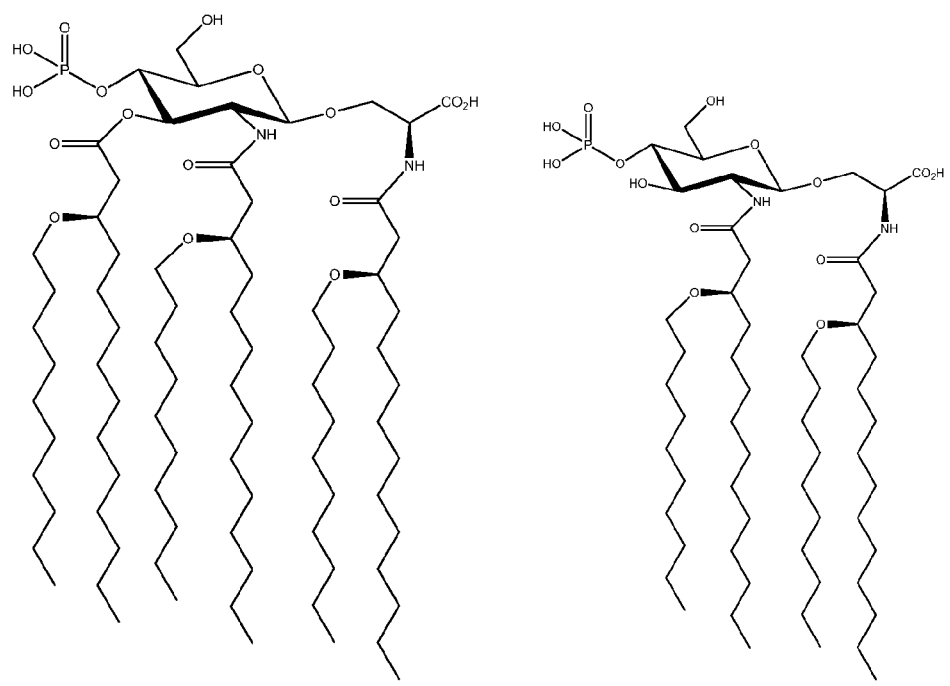
FIG. 1 shows the structure of CRX-601 and the CRX-601 degradant from the examples.

Aminoalkyl Glucosaminide Phosphate Compounds.

AGPs are Toll-Like Receptor 4 (TLR4) modulators. Toll-like receptor 4 recognizes bacterial LPS (lipopolysaccharide) and when activated initiates an innate immune response. AGPs are a monosaccharide mimetic of the lipid A protein of bacterial LPS and have been developed with ether and ester linkages on the "acyl chains" of the compound. Processes for making these compounds are known and disclosed, for example, in WO 2006/016997, U.S. Pat. Nos. 7,288,640 and 6,113,918, and WO 01/90129, which are hereby incorporated by reference in their entireties. Other AGPs and related processes are disclosed in U.S. Pat. No. 7,129,219, U.S. Pat. No. 6,525,028 and U.S. Pat. No. 6,911,434. AGPs with ether linkages on the acyl chains employed in the composition of the invention are known and disclosed in WO 2006/016997 which is hereby incorporated by reference in its entirety. Of particular interest, are the aminoalkyl glucosaminide phosphate compounds set forth and described according to Formula (III) at paragraphs [0019] through [0021] in WO 2006/016997.

Aminoalkyl glucosaminide phosphate compounds employed in the present invention have the structure set forth in Formula 1 as follows:

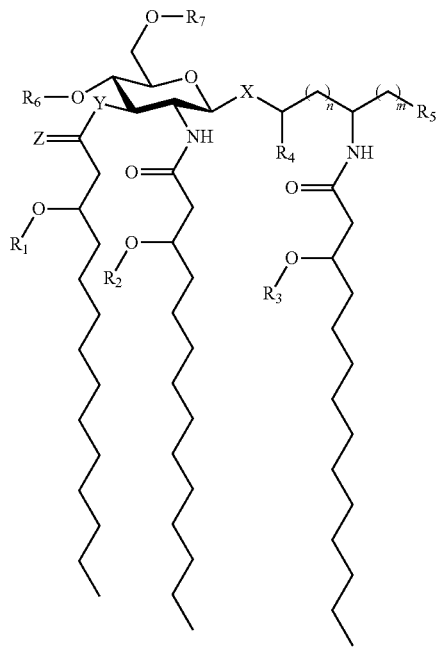

(Formula 1)

wherein m is 0 to 6 n is 0 to 4;

X is O or S, preferably O;

Y is O or NH;

Z is O or H;

each $R_1$, $R_2$, $R_3$ is selected independently from the group consisting of a $C_{1-20}$ acyl and a $C_{1-20}$ alkyl;

$R_4$ is H or Me;

$R_5$ is selected independently from the group consisting of —H, —OH, —($C_1$-$C_4$) alkoxy, —$PO_3R_8R_9$, —$OPO_3R_8R_9$, —$SO_3R_8$, —$OSO_3R_8$, —$NR_8R_9$, —$SR_8$, —CN, —$NO_2$, —CHO, —$CO_2R_8$, and —$CONR_8R_9$, wherein $R_8$ and $R_9$ are each independently selected from H and ($C_1$-$C_4$) alkyl; and each $R_6$ and $R_7$ is independently H or $PO_3H_2$.

In Formula 1 the configuration of the 3' stereogenic centers to which the normal fatty acyl residues (that is, the secondary acyloxy or alkoxy residues, e.g., $R_1O$, $R_2O$, and $R_3O$) are attached is R or S, preferably R (as designated by Cahn-Ingold-Prelog priority rules). Configuration of aglycon stereogenic centers to which $R_4$ and $R_5$ are attached can be R or S. All stereoisomers, both enantiomers and diastereomers, and mixtures thereof, are considered to fall within the scope of the present invention.

The number of carbon atoms between heteroatom X and the aglycon nitrogen atom is determined by the variable "n", which can be an integer from 0 to 4, preferably an integer from 0 to 2.

The chain length of normal fatty acids $R_1$, $R_2$, and $R_3$ can be from about 6 to about 16 carbons, preferably from about 9 to about 14 carbons. The chain lengths can be the same or different. Some preferred embodiments include chain lengths where R1, R2 and R3 are 6 or 10 or 12 or 14.

Formula 1 encompasses L/D-seryl, -threonyl, -cysteinyl ether and ester lipid AGPs, both agonists and antagonists and their homologs (n=1-4), as well as various carboxylic acid bioisosteres (i.e, $R_5$ is an acidic group capable of salt formation; the phosphate can be either on 4- or 6-position of the glucosamine unit, but preferably is in the 4-position).

In a preferred embodiment of the invention employing an AGP compound of Formula 1, n is 0, $R_5$ is $CO_2H$, $R_6$ is $PO_3H_2$, and $R_7$ is H. This preferred AGP compound is set forth as the structure in Formula 1a as follows:

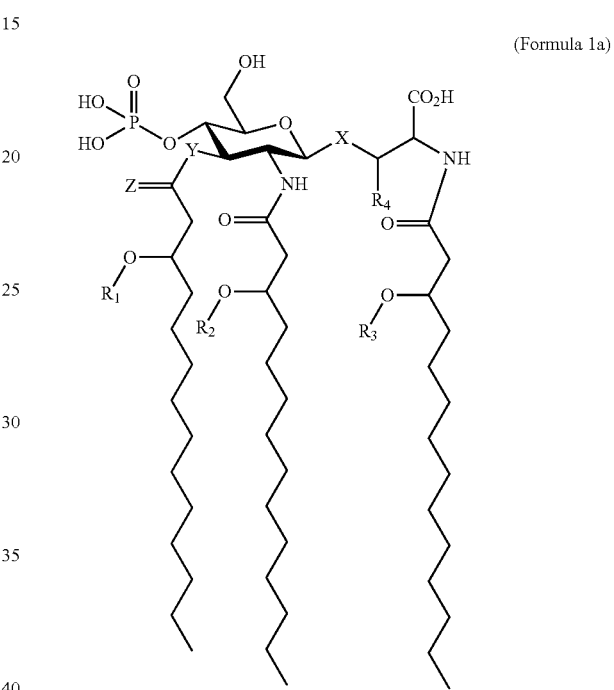

(Formula 1a)

wherein X is O or S; Y is O or NH; Z is O or H; each $R_1$, $R_2$, $R_3$ is selected independently from the group consisting of a $C_{1-20}$ acyl and a $C_{1-20}$ alkyl; and $R_4$ is H or methyl.

In Formula 1a the configuration of the 3' stereogenic centers to which the normal fatty acyl residues (that is, the secondary acyloxy or alkoxy residues, e.g., $R_1O$, $R_2O$, and $R_3O$) are attached as R or S, preferably R (as designated by Cahn-Ingold-Prelog priority rules). Configuration of aglycon stereogenic centers to which $R_4$ and $CO_2H$ are attached can be R or S. All stereoisomers, both enantiomers and diastereomers, and mixtures thereof, are considered to fall within the scope of the present invention.

Formula 1a encompasses L/D-seryl, -threonyl, -cysteinyl ether or ester lipid AGPs, both agonists and antagonists.

In both Formula 1 and Formula 1a, Z is O attached by a double bond or two hydrogen atoms which are each attached by a single bond. That is, the compound is ester-linked when Z=Y=O; amide-linked when Z=O and Y=NH; and ether-linked when Z=H/H and Y=O.

Especially preferred compounds of Formula 1 are referred to as CRX-601 and CRX-527. Their structures are set forth as follows:

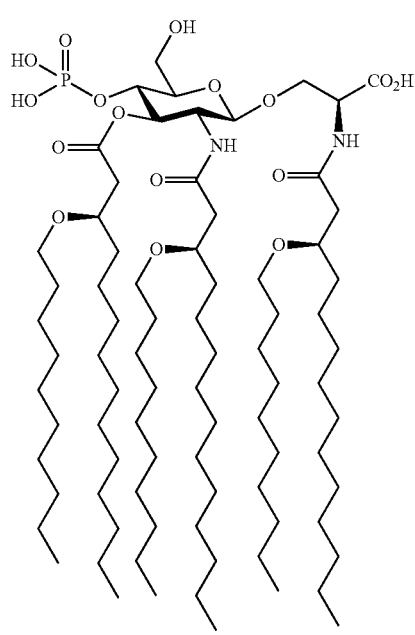
(CRX-601)
Additionally, another preferred embodiment employs CRX 547 having the structure shown.
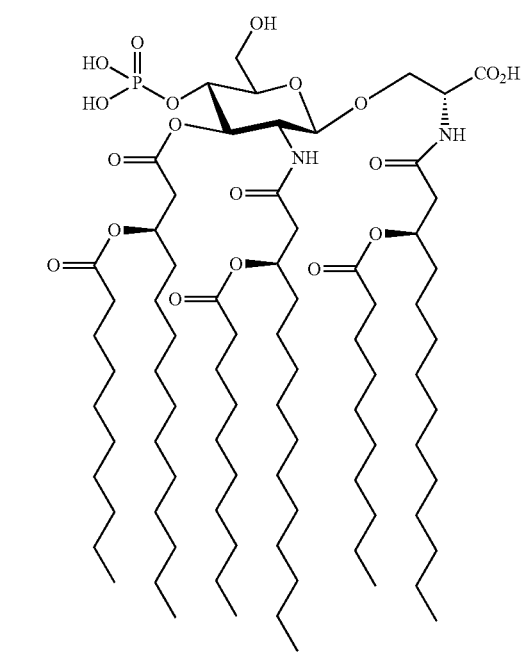
CRX 547
Still other embodiments include AGPs such as CRX 602 or CRX 526 providing increased stability to AGPs having shorter secondary acyl or alkyl chains.
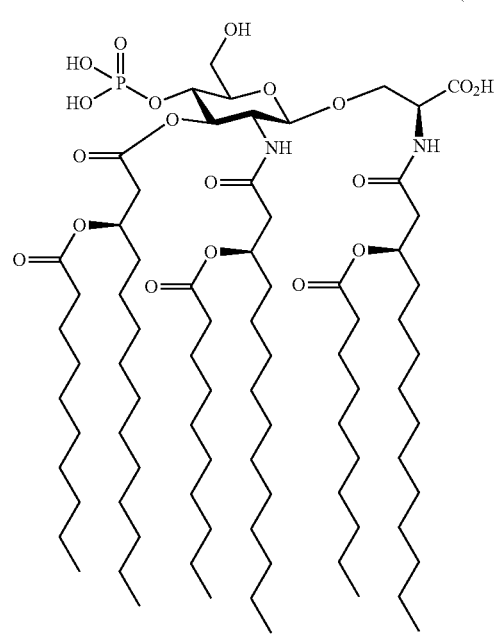
(CRX-527)
CRX 602

-continued

CRX-526

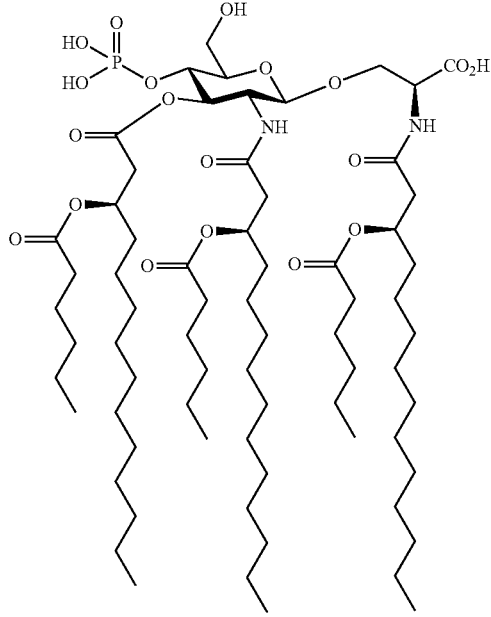

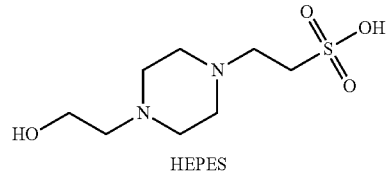 [SMILES: O=S(=O)(O)CCN1CCN(CCO)CC1]

HEPES

Buffers.

In one embodiment of the present invention, the composition comprising an AGP is buffered using a zwitterionoic buffer. Suitably, the zwitterionic buffer is an aminoalkanesulfonic acid or suitable salt. Examples of aminoalkanesulfonic buffers include but are not limited to HEPES, HEPPS/EPPS, MOPS, MOBS and PIPES. Preferably, the buffer is a pharmaceutically acceptable buffer, suitable for use in humans, such as in for use in a commercial injection product. Most preferably the buffer is HEPES.

In suitable embodiments of the present invention the AGPs are buffered using a buffer selected from the group consisting of:

i) HEPES having a pH of about 7, ii) citrate (e.g., sodium citrate) having a pH of about 5, and iii) acetate (e.g., ammonium acetate) having a pH of about 5.

In a preferred embodiment of the present invention the AGPs CRX-601, CRX-527 and CRX-547 are buffered using HEPES having a pH of about 7. The buffers may be used with an appropriate amount of saline or other excipient to achieve desired isotonicity. In one preferred embodiment 0.9% saline is used.

HEPES: CAS Registry Number: 7365-45-9 $C_8H_{18}N_2O_4S$

1-Piperazineethanesulfonic acid, 4-(2-hydroxyethyl)-

HEPES is a zwitterionic buffer designed to buffer in the physiological pH range of about 6 to about 8 (e.g. 6.15-8.35) and more specifically from a more useful range of about 6.8 to about 8.2 and, as in the present invention, between about 7 and about 8 or between 7 and 8, and preferably between about 7 and less than 8. HEPES is typically a white crystalline powder and has the molecular formula: $C_8H_{18}N_2O_4S$ of the following structure:

HEPES is well-known and commercially available. (See, for example, Good et al., Biochemistry 1966.)

The citrate buffer (e.g., sodium citrate) and acetate when employed as the buffer in the composition of the invention both have a pH of about 5. In one embodiment the concentration of the buffer is about 10 mM, but in some embodiments an increased buffer concentration may be needed. The citrate and acetate buffers may be employed in the compositions of the invention with AGPs that require an acidic or slightly acidic pH. Acetate buffer works well in environments or compositions in which citrate buffers may not be used, such as in the presence of alum. Citrate and acetate buffers are commercially available.

Nanoparticulate Mixture/Solution.

When formed, the composition of the invention may be a dispersion or solution. Suitably, the composition is a nanoparticulate solution with particle sizes of ≤200 nm. In one suitable embodiment the composition is a nanoparticulate solution with particle sizes of ≤200 nm displaying micellar or liposomal characteristics. In one embodiment the solution or dispersion is suitable for pharmaceutical use as an immunomodulator. The size of particulates in solution is determined in part by the length of time the composition in the solution or dispersion is subjected to sonication.

Method of Treatment and Administration.

The present invention provides a method for enhancing an immune response of a subject comprising administering to the subject an effective amount of the pharmaceutical composition.

The compositions of the present invention may be used to protect or treat a mammal by means of administering via systemic or mucosal route. These administrations may include injection via the intramuscular, intraperitoneal, intradermal or subcutaneous routes; or via mucosal administration to the oral/alimentary, respiratory, genitourinary tracts. The composition of the invention may be administered as a single dose, or multiple doses. In addition, the compositions of the invention may be administered by different routes for priming and boosting, for example, IM priming doses and IN for booster doses.

The composition of the present invention may be administered alone or with suitable pharmaceutical carriers, and can be used in the manufacture of solid or liquid form, such as tablets, capsules, powders, solutions, suspensions, or emulsions. The composition may be formulated into a "vaccine," and administered in free solution, or formulated with an adjuvant, or excipient. Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877. The vaccines may be stored in solution or lyophilized.

Effective doses of treatments which incorporate the compositions of the present invention for the treatment of a subject vary depending upon many different factors, including means of administration, target site, physiological state of the patient, other medications administered, physical state of the patient relative to other medical complications, and whether treatment is prophylactic or therapeutic. Treatment dosages need to be titrated to optimize safety and efficacy. Subject doses described herein typically range from about 0.1 µg to 50 mg per administration which depending on the application could be given daily, weekly, or monthly and any other amount of time there between. More typically mucosal or local doses range from about 10 µg to 10 mg per administration, and optionally from about 100 µg to 1 mg, with 2-4 administrations being spaced days or weeks apart. More typically, immune stimulant doses range from 1 µg to 10 mg per administration, and most typically 10 µg to 1 mg, with daily or weekly administrations. Doses incorporating the invention described herein for parenteral delivery e.g., for inducing an innate immune response, or in specialized delivery vehicles typically range from about 0.1 µg to 10 mg per administration, which depending on the application could be given daily, weekly, or monthly and any other amount of time there between. More typically parenteral doses for these purposes range from about 10 µg to 5 mg per administration, and most typically from about 100 µg to 1 mg, with 2-4 administrations being spaced days or weeks apart. In some embodiments, however, parenteral doses for these purposes may be used in a range of 5 to 10,000 times higher than the typical doses described above.

There is also provided a method for ameliorating or substantially preventing an infectious disease, an autoimmune disease, neurological disorder or an allergic or inflammatory condition in a subject comprising administering to the subject an effective amount of the pharmaceutical composition. In some instances, an exogenous antigen may be administered to the subject along with the pharmaceutical composition. In compositions for eliciting or enhancing an immune response, the compositions of the subject invention are administered to a warm-blooded animal, such as a human or other mammal, with an antigen such as a protein or polypeptide antigen or a polynucleotide that expresses a protein or polypeptide antigen. The amount of antigen administered to elicit a desired response can be readily determined by one skilled in the art and will vary with the type of antigen administered, route of administration and immunization schedule. The compositions of the present invention can also be administered without an exogenous antigen, to elicit immediate protection via a non-specific resistance effect. Compositions having the ability to stimulate non-specific resistance and/or elicit an adjuvant effect can be used in rapid acting vaccine formulations.

Terms/Definitions

As discussed herein, the term "aliphatic" by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ or $C_{1-10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated aliphatic group is one having one or more double bonds or triple bonds. Examples of unsaturated aliphatic groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Typically, an aliphatic group will have from 1 to 24 carbon atoms. A "lower aliphatic" group is a shorter chain aliphatic group, generally having eight or fewer carbon atoms.

The term "acyl" refers to a group derived from an organic acid by removal of the hydroxy group. Examples of acyl groups include acetyl, propionyl, dodecanoyl, tetradecanoyl, isobutyryl, and the like. Accordingly, the term "acyl" as used herein is meant to include a group otherwise defined as —C(O)-aliphatic, where the aliphatic group is preferably a saturated aliphatic group.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. In one embodiment, the salt is an ethanolamine salt, such as monoethanolamine (MEA) or triethanolamine (TEA). When compounds used in the composition of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al, "Pharmaceutical Salts," *Journal of Pharmaceutical Science*, 66, 1-19, 1977). Certain specific compounds used in the composition of the present invention contain both basic and acidic functionalities that allow the compounds to be converted into either base or acid addition salts.

As used herein, "pharmaceutically acceptable carrier" means a medium that does not interfere with the immunomodulatory activity of the active ingredient and is not toxic to the patient to whom it is administered.

Pharmaceutically acceptable carriers include oil-in-water or water-in-oil emulsions, multiple emulsions (e.g. water in oil in water), micro-emulsions, liposomes, microbeads, microspheres, microsomes and the like. For example, the carrier may be a microsphere or preferably a nanoshpere, or may be a microparticle or preferably a nanoparticle, having a compound of this invention within the matrix of the sphere or particle or adsorbed on the surface of the sphere or particle. The carrier may also be an aqueous solution or micellar dispersion containing triethylamine, triethanolamine or other agent that renders the formulation alkaline in nature, or a suspension containing aluminum hydroxide, calcium hydroxide, calcium phosphate or tyrosine adsorbate. Carriers may also include all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like.

The formation and use of liposome and liposome-like preparations as potential drug carriers is generally known to those of skill in the art (see for example, Lasic, Trends Biotechnol 1998 July; 16(7):307-21; Takakura, Nippon Rinsho 1998 March; 56(3):691-5; Chandran et al., Indian J Exp Biol. 1997 August; 35(8):801-9; Margalit, Crit Rev Ther Drug Carrier Syst. 1995; 12(2-3):233-61; U.S. Pat. No. 5,567,434; U.S. Pat. No. 5,552,157; U.S. Pat. No. 5,565,213; U.S. Pat. No. 5,738,868 and U.S. Pat. No. 5,795,587).

Liposomes have been used successfully with a number of cell types that are normally difficult to transfect by other procedures, including T cell suspensions, primary hepatocyte cultures and PC 12 cells (Renneisen et al., J Biol Chem. 1990 Sep. 25; 265(27):16337-42; Muller et al., DNA Cell Biol. 1990 April; 9(3):221-9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. 1998 December; 24(12):1113-28). To avoid side effects due to intracellular polymeric overloading, such ultrafine particles (sized around 0.1 µm) may be designed using polymers able to be degraded in vivo. Such particles can be made as described, for example, by Couvreur et al., Crit Rev Ther Drug Carrier Syst. 1988; 5(1):1-20; zur Muhlen et al., Eur J Pharm Biopharm. 1998 March; 45(2):149-55; Zambaux et al. J Controlled Release. 1998 Jan. 2; 50(1-3):31-40; and U.S. Pat. No. 5,145,684.

The term "immunomodulator" as used herein means a substance that alters the immune response in a subject, such as by augmenting, reducing, changing or otherwise affecting the subject's immune response.

Routes of Administration

Compositions of the subject invention that can be administered parenterally, i.e. intraperitoneally, subcutaneously or intramuscularly include the following preferred carriers. Examples of suitable carriers for subcutaneous use include but are not limited to a phosphate buffered saline (PBS) solution, or 0.9% sodium chloride in USP Water for Injection, and 0.01-0.1% triethanolamine in USP Water for Injection. Suitable carriers for intramuscular injection include but are not limited to 10% USP ethanol, 40% propylene glycol and the balance an acceptable isotonic solution such as 5% dextrose, or 0.9% sodium chloride in USP Water for Injection. Examples of suitable carriers for intravenous use include but are not limited to 10% USP ethanol, 40% USP propylene glycol and the balance USP Water for Injection, or 0.9% sodium chloride in USP Water for Injection. In one embodiment the carrier includes 10% USP ethanol and USP Water for Injection; for yet another embodiment the acceptable carrier is 0.01-0.1% triethanolamine in USP Water for Injection. Pharmaceutically acceptable parenteral solvents are such as to provide a solution or dispersion may be filtered through a 5 micron filter, or preferably a 0.2 micron filter, without removing the active ingredient.

Another route of administration of the compositions of this invention is mucosal administration, particularly intranasal administration or in some cases administration by inhalation (pulmonary administration). Pulmonary drug delivery can be achieved by several different approaches, including liquid nebulizers, aerosol-based metered dose inhalers (MDIs), and dry powder dispersion devices. Compositions for use in administrations of this type are typically dry powders or aerosols.

Dry powders contain, in addition to the composition of the invention, a carrier, an absorption enhancer, and optionally other ingredients. The carrier is, for example, a mono-, di- or polysaccharide, a sugar alcohol or another polyol. Suitable carriers include lactose, glucose, raffinose, melezitose, lactitol, maltitol, trehalose, sucrose, mannitol; and starch. Lactose is particularly preferred, especially in the form of its monohydrate. Also included are absorption enhancers such as polypeptides, surfactants, alkyl glycosides, amine salts of fatty acids or phospholipids. The ingredients of the formulation typically must be in a finely divided form, i.e. their volume median diameter should generally be from about 30 to about 200 microns, as measured by a laser diffraction instrument or a coulter counter. The desired particle size may be produced using methods known in the art, e.g. milling, micronization or direct precipitation.

The intranasal route of administration provides numerous advantages over many other forms of administration for the compounds of this invention. For instance, one advantage of intranasal administration is convenience. An injectable system requires sterilization of the hypodermic syringe and in the institutional setting, leads to concerns among medical personnel about the risk of contracting disease by being accidentally stuck by a contaminated needle. Strict requirements for the safe disposal of the used needle and syringe must also be imposed in the institutional setting. In contrast, intranasal administration requires little time on the part of the patient and the attending medical personnel, and is far less burdensome on the institution than injectables.

A second important advantage of intranasal administration is patient acceptance of the drug delivery system. Intranasal administration is perceived as non-invasive, is not accompanied by pain, has no significant after-effects and produces the gratification of prompt relief in the patient exhibiting the symptom. This is of particular advantage when the patient is a child. Another important consideration is that the patient may be able to self-administer the prescribed dosage(s) of nasal spray.

For intranasal administration the compositions of this invention may be formulated as liquids or as solids. Such formulations may contain one or more additional adjuvants, agents for enhancing absorption of the active ingredients by permeation across the nasal membrane, and (for liquid compositions) an additional aqueous buffer or other pharmaceutically acceptable carriers. The composition may further optionally include one or more polyhydric alcohols and one or more preservative agents. Suitable preservatives include, for example, gentamicin, bacitracin (0.005%), or cresol. The compositions may be administered to the nasal cavity in the form of a spray by using an atomizer, nebulizer, sprayer, dropper or other device which insures contact of the solution with the nasal mucous membrane. The device may be a simple one such as a simple nasal sprayer that may be used by the patient, or may be a more elaborate instrument for more accurate dispensing of the compositions, that may be used in a physician's office or a medical facility.

Nasal powder compositions can be made by lyophilizing the composition of the present invention or adsorbing the composition onto suitable nasal powders (e.g. lactose) and milling if needed to the desired particle size. Alternatively, a solution of the composition and cyclodextrin excipients can be made, followed by precipitation, filtration and pulverization. It is also possible to remove the solvent by freeze drying, followed by pulverization of the powder in the desired particle size by using conventional techniques, known from the pharmaceutical literature. The final step is size classification for instance by sieving, to get particles that are preferably between 30 and 200 microns in diameter. Powders can be administered using a nasal insufflator, or they may be placed in a capsule set in an inhalation or insufflation device. A needle is penetrated through the capsule to make pores at the top and the bottom of the capsule and air is sent to blow out the powder particles. Powder formulation can also be administered in a jet-spray of an inert gas or suspended in liquid organic fluids.

The compositions of the subject invention are administered to an individual in an effective amount or a pharmaceutically effective amount, to effect or enhance the individual's immune response. As used herein, "effective amount" or "pharmaceutically effective amount" is that amount which shows a response over and above the vehicle or negative controls. An "adjuvant-effective amount" is that amount of the compound in question that, when administered in conjunction with an antigen, shows a response over and above that produced by the antigen alone. The precise dosage of the composition of the subject invention to be administered to a patient will depend upon the particular compound used, the route of administration, the pharmaceutical composition, and the patient.

MM6 Potency Assay

The MonoMac6 Potency assay is used to quantitatively measure the relative potency between two different lots of a biological product. A dose range of test and reference compounds are co-incubated with MonoMac6 cells, a human monocytic cell line, and cell supernatants are harvested for further testing. A chemokine marker (MIP-1β), measured from the cell supernatants by a nested ELISA, serves as readout. A potency analysis template was constructed into which raw optical densities are pasted, and analysis is automatically performed. Based on the slope and the parallelism between the test and reference response curves, set criteria within the defined metrics determine whether or not a successful potency determination can occur. If these criteria are successfully met, the analysis will yield a relative potency value of the test product against the reference product.

The present invention is further described by way of the following non-limiting Examples and Testing Examples that are given for illustrative purposes only. All references cited herein are incorporated by reference in their entirety.

EXPERIMENTAL

Example 1: Formulating HEPES at pH=7.0

The molecular weight of HEPES is 238.3 g/mol. Thus, 6.044 g of HEPES was weighed and 200 mL of sterile water was added and the mixture was stirred using a magnetic stirrer. The pH of the solution was measured to be 5.2. Then 5 N NaOH was added dropwise to achieve a final pH of 7.0. The volume of the solution was made up to 250 mL resulting in a 100 mM HEPES buffer at pH=7.0. This buffer was sterile filtered for future use. To prepare the 10 mM HEPES buffer, 10 mL of the 100 mM HEPES buffer was diluted into 90 mL of sterile water (total volume=100 mL). The resulting 10 mM HEPES buffer at pH=7.0 was also sterile filtered to be used with CRX-601 which was obtained from GSK Vaccines Hamilton, Mont.

Example 2 (Comparative): Formulating HEPES at pH=8.0

The molecular weight of HEPES is 238.3 g/mol. Thus, 6.044 g of HEPES was weighed and 200 mL of sterile water was added and the mixture was stirred using a magnetic stirrer. The pH of the solution was measured to be 5.2. Then 5 N NaOH was added dropwise to achieve a final pH of 8.0. The volume of the solution was made up to 250 mL resulting in a 100 mM HEPES buffer at pH=8.0. This buffer was sterile filtered for future use. To prepare the 10 mM HEPES buffer, 10 mL of the 100 mM HEPES buffer was diluted into 90 mL of sterile water (total volume=100 mL). The resulting 10 mM HEPES buffer at pH=8.0 was also sterile filtered to be used with CRX-601.

Example 3: Formulating AGPs and HEPES at pH=7.0

CRX-601 was formulated in the 10 mM HEPES buffered at pH=7.0 at 2 mg/mL target concentration by weighing 3.99 mg of CRX-601 and adding 1.877 mL of 10 mM HEPES followed by ultrasonication in a water bath sonicator. After 25 minutes the solution was visibly clear, but the sonication was continued since the other CRX-601 formulations with the other buffers employed herein had not yet achieved similar visual appearance. This was done because the goal was to subject each CRX-601 buffered formulation to the same amount of processing energy.

Example 4 (Comparative): Formulating AGPs and HEPES at pH=8

CRX-601 was formulated in the 10 mM HEPES buffered at pH=8.0 at 2 mg/mL target concentration by weighing 3.99 mg of CRX-601 and adding 1.877 mL of 10 mM HEPES followed by ultrasonication in a water bath sonicator. After 25 minutes the solution was visibly clear, but the sonication was continued since the other CRX-601 formulations with the other buffers employed herein had not yet achieved similar visual appearance. This was done because the goal was to subject each CRX-601 buffered formulation to the same amount of processing energy.

Formulating the Non-HEPES Buffers.

The pH for each buffer was within the buffering capacity for the respective buffer. The preparation recipe for each buffer is described below.

Example 5: Acetate Buffer at pH=5.0

The molecular weight of ammonium acetate is 77.08 g/mol. Thus, 1.927 g of ammonium acetate was weighed and 200 mL of sterile water was added and the mixture was stirred using a magnetic stirrer. The pH of the solution was measured to be 6.6. Then acetic acid was added dropwise to achieve a final pH of 5.0. The volume of the solution was made up to 250 mL resulting in a 100 mM acetate buffer at pH=5.0. This buffer was sterile filtered for future use. To prepare the 10 mM acetate buffer, 10 mL of the 100 mM acetate buffer was diluted into 90 mL of sterile water (total volume=100 mL). The resulting 10 mM acetate buffer at pH=5.0 was also sterile filtered to be used with CRX-601.

Example 6 (Comparative): Acetate Buffer at pH=5.5

The molecular weight of ammonium acetate is 77.08 g/mol. Thus, 1.927 g of ammonium acetate was weighed and 200 mL of sterile water was added and the mixture was stirred using a magnetic stirrer. The pH of the solution was measured to be 6.6. Then acetic acid was added drop wise to achieve a final pH of 5.5. The volume of the solution was made up to 250 mL resulting in a 100 mM acetate buffer at pH=5.5. This buffer was sterile filtered for future use. To prepare the 10 mM acetate buffer, 10 mL of the 100 mM acetate buffer was diluted into 90 mL of sterile water (total volume=100 mL). The resulting 10 mM acetate buffer at pH=5.5 was also sterile filtered to be used with CRX-601.

Example 7: Citrate Buffer at pH=5.0

The molecular weight of trisodium citrate (dehydrate) is 294.1 g/mol and citric acid (monohydrate) is 210.14 g/mol. Thus, 3.670 g of trisodium citrate and 2.627 of citric acid were weighed and 200 mL of sterile water was added and the mixture was stirred using a magnetic stirrer. The pH of the solution was measured to be 4.1. Then 5 N NaOH was added dropwise to achieve a final pH of 5.0. The volume of the solution was made up to 250 mL resulting in a 100 mM citrate buffer at pH=5.0. This buffer was sterile filtered for future use. To prepare the 10 mM citrate buffer, 10 mL of the 100 mM citrate buffer was diluted into 90 mL of sterile water (total volume=100 mL). The resulting 10 mM citrate buffer at pH=5.0 was also sterile filtered to be used with CRX-601.

Example 8 (Comparative): Citrate Buffer at pH=6.0

The molecular weight of trisodium citrate (dehydrate) is 294.1 g/mol and citric acid (monohydrate) is 210.14 g/mol. Thus, 3.670 g of trisodium citrate and 2.627 g of citric acid were weighed and 200 mL of sterile water was added and the mixture was stirred using a magnetic stirrer. The pH of the solution was measured to be 4.1. Then 5 N NaOH was added dropwise to achieve a final pH of 6.0. The volume of the solution was made up to 250 mL resulting in a 100 mM citrate buffer at pH=6.0. This buffer was sterile filtered for future use. To prepare the 10 mM citrate buffer, 10 mL of the 100 mM citrate buffer was diluted into 90 mL of sterile water (total volume=100 mL). The resulting 10 mM citrate buffer at pH=6.0 was also sterile filtered to be used with CRX-601.

Example 9 (Comparative): Citrate Buffer at pH=6.1

The molecular weight of trisodium citrate (dehydrate) is 294.1 g/mol and citric acid (monohydrate) is 210.14 g/mol. Thus, 3.670 g of trisodium citrate and 2.627 g of citric acid were weighed and 200 mL of sterile water was added and the mixture was stirred using a magnetic stirrer. The pH of the solution was measured to be 4.1. Then 5 N NaOH was added dropwise to achieve a final pH of 6.1. The volume of the solution was made up to 250 mL resulting in a 100 mM citrate buffer at pH=6.1. This buffer was sterile filtered for future use. To prepare the 10 mM citrate buffer, 10 mL of the 100 mM citrate buffer was diluted into 90 mL of sterile water (total volume=100 mL). The resulting 10 mM citrate buffer at pH=6.1 was also sterile filtered to be used with CRX-601.

Example 10 (Comparative): Citrate Buffer at pH=7.0

The molecular weight of trisodium citrate (dehydrate) is 294.1 g/mol and citric acid (monohydrate) is 210.14 g/mol. Thus 3.670 g of trisodium citrate and 2.627 g of citric acid were weighed and 200 mL of sterile water was added and the mixture was stirred using a magnetic stirrer. The pH of the solution was measured to be 4.1. Then 5 N NaOH was added dropwise to achieve a final pH of 7.0. The volume of the solution was made up to 250 mL resulting in a 100 mM citrate buffer at pH=7.0. This buffer was sterile filtered for future use. To prepare the 10 mM citrate buffer, 10 mL of the 100 mM citrate buffer was diluted into 90 mL of sterile water (total volume=100 mL). The resulting 10 mM citrate buffer at pH=7.0 was also sterile filtered to be used with CRX-601.

Example 11 (Comparative): TRIS Buffer at pH=7.0

The molecular weight of TRIS is 121.14 g/mol. Thus, 3.029 g of TRIS was weighed and 200 mL of sterile water was added and the mixture was stirred using a magnetic stirrer. The pH of the solution was measured to be 10.5. Then 6 N HCl was added dropwise to achieve a final pH of 7.0. The volume of the solution was made up to 250 mL resulting in a 100 mM TRIS buffer at pH=7.0. This buffer was sterile filtered for future use. To prepare the 10 mM TRIS buffer, 10 mL of the 100 mM citrate buffer was diluted into 90 mL of sterile water (total volume=100 mL). The resulting 10 mM TRIS buffer at pH=7.0 was also sterile filtered to be used with CRX-601.

Example 12 (Comparative): Succinate Buffer at pH=7.0

The molecular weight of succinic anhydride is 100.07 g/mol. Thus, 2.502 g of succinic anhydride was weighed and 200 mL of sterile water was added and the mixture was stirred using a magnetic stirrer. The pH of the solution was measured to be 2.5. Then 5 N NaOH was added dropwise to achieve a final pH of 7.0. The volume of the solution was made up to 250 mL resulting in a 100 mM succinate buffer at pH=7.0. This buffer was sterile filtered for future use. To prepare the 10 mM succinate buffer, 10 mL of the 100 mM succinate buffer was diluted into 90 mL of sterile water (total volume=100 mL). The resulting 10 mM succinate buffer at pH=7.0 was also sterile filtered to be used with CRX-601.

Example 13 (Comparative): Phosphate Buffer at pH=7.0

The molecular weight of sodium phosphate (monobasic) is 137.99 g/mol and sodium phosphate (dibasic) is 141.96 g/mol. Thus, 0.059 g of sodium phosphate (monobasic) and 0.082 g of sodium phosphate (dibasic) were weighed and 80 mL of sterile water was added and the mixture was stirred using a magnetic stirrer. The pH of the solution was measured to be 7.0. The volume of the solution was made up to 100 mL resulting in a 10 mM phosphate buffer at pH=7.0. This buffer was sterile filtered for future use with CRX-601.

Example 14 (Comparative): Sodium Phosphate Buffer at pH=6.1

The molecular weight of sodium phosphate (dibasic) is 141.96 g/mol and sodium chloride is 58.5 g/mol. Thus, 7.098 g of sodium phosphate (dibasic) and 5.844 g of sodium chloride was weighed and 900 mL of sterile water was added and the mixture was stirred using a magnetic stirrer. The pH of the solution was measured to be 9.0. Then 6 N HCl was added dropwise to achieve a final pH of 6.1. The volume of the solution was made up to 1000 mL resulting in a 100 mM NaCl and 50 mM sodium phosphate (dibasic) buffer at pH=6.1. This buffer was sterile filtered for future use with CRX-601.

Example 15

Formulating AGPs and Buffers

Table 1 lists seven common buffers regarded as being useful in the pharmaceutical arts. CRX-601 was formulated in each of the buffers summarized in Table 1 at a target concentration of 2 mg/mL. The buffers were formulated at or near their reported optimal pH shown in Table 1.

All the samples were processed under the same conditions to quantify the degradation of CRX-601 caused due to the specific buffer and not due to processing except for CRX-601 in acetate buffer which took longer to process.

TABLE 1

| | Buffer | components | pH | Conc. (mM) | pKa(s) | Reference to text |
|---|---|---|---|---|---|---|
| 1 | HEPES | 4-(2-hydroxyethyl)-1-piperazineethanesulfonic acid | 7.0 | 10 | 3, 7.6 | Example 1 |
| 2 | Citrate | Sodium citrate (Citric acid) | 6.1 | 10 | 3.1, 4.8, 6.3 | Example 9 |
| 3 | Phosphate | Sodium phosphate monobasic and diabasic | 7.0 | 10 | 2.1, 7.0, 12.3 | Example 13 |
| 4 | Succinate | Succinic anhydride | 7.0 | 10 | 4.2, 5.6 | Example 12 |
| 5 | TRIS | Amino-2-hydroxymethyl-methane (HCl) | 7.1 | 10 | 8.3 | Example 11 |
| 6 | Ammonium Acetate | Ammonium acetate (Acetic acid) | 5.5 | 10 | 4.7, 9.2 | Example 6 |
| 7 | Phosphate | Sodium Phosphate, NaCl | 6.1 | 50 | 7.2 | Example 14 |

Each of the buffer solutions was then sonciated to reduce the particle size to allow for sterile filtration. Table 2 shows the processing time to achieve a partially clear solution (i.e. achieve a particle size of approximately 200 nm) by sonication for each of the CRX-601 buffered formulations.

TABLE 2

| | Buffers | pH of the buffer | Visual appearance to clear solution (minutes) |
|---|---|---|---|
| 1 | HEPES 10 mM | 7.00 | 25 |
| 2 | Sodium Citrate 10 mM | 6.10 | 60 |
| 3 | Sodium Phosphate 10 mM | 7.15 | 15 |
| 4 | Sodium Succinate 10 mM | 7.00 | 35 |
| 5 | TRIS Chloride 10 mM | 7.10 | 60 |
| 6 | Ammonium Acetate 10 mM | 5.50 | 160 |
| 7 | Sodium Phosphate 0.1M in 0.5M saline (LBH) | 6.10 | 80 |

Degradation

Figure 2:
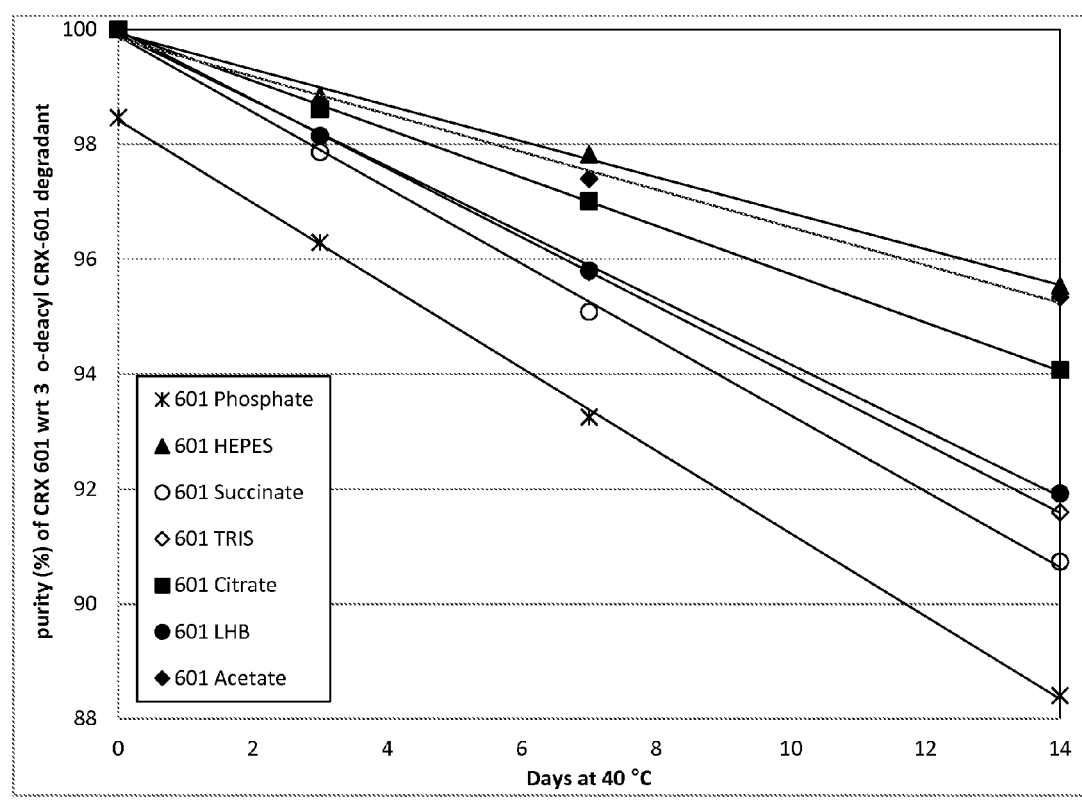
FIG. 2 shows the accelerated rate of degradation for buffers formulated with CRX-601 at a neutral or near physiological pH.

Buffers 1-7 of Table 1 were screened for stability at the concentrations shown in the Table using an accelerated stability test. The buffer compositions were maintained for 14 days at 40° C. The stability of CRX-601 in each composition was determined by measuring the percent of CRX-601 in the composition with respect to common CRX-601 degradant (structures shown in FIG. 1). The plot in FIG. 2 shows the data from the first set of buffers that were screened with CRX-601. The slope of the trend lines fitted to each data series is a measure of the rate of degradation of CRX-601. Interestingly HEPES (pH=7.00), acetate (pH=5.50), and citrate (pH=6.10) were found to cause least degradation of CRX-601 in solution after 14 days at 40° C. Sodium phosphate (ph=7.15), succinate (pH=7.00), TRIS (pH=7.10) and sodium phosphate (pH=6.10) showed reduced stability, and surprisingly reduced stability compared to HEPES (pH=7). No significant changes in pH were observed during the study. The particle size for all the formulations remained stable except for CRX-601 in Liposome Hydration Buffer (LHB) and acetate buffer which showed aggregation.

Example 16

Stability/Purity

Buffers were evaluated to identify the effect of pH on the rate of degradation of CRX-601; specifically the stability of CXR-601 formulated in acetate at pH=5.0, HEPES at pH 7.0, 8.0, and citrate at 5.0, 6.0 and 7.0 were tested. To this end, the following buffers: HEPES at pH 7.0, 8.0, citrate at pH 5.0, 6.0, 7.0, and acetate at pH=5.0 were prepared according to the Examples 1, 2, 5, 7, 8, and 10 and CRX-601 was formulated in each of them and subjected to forced degradation for 14 days at 40° C.

Figure 3:
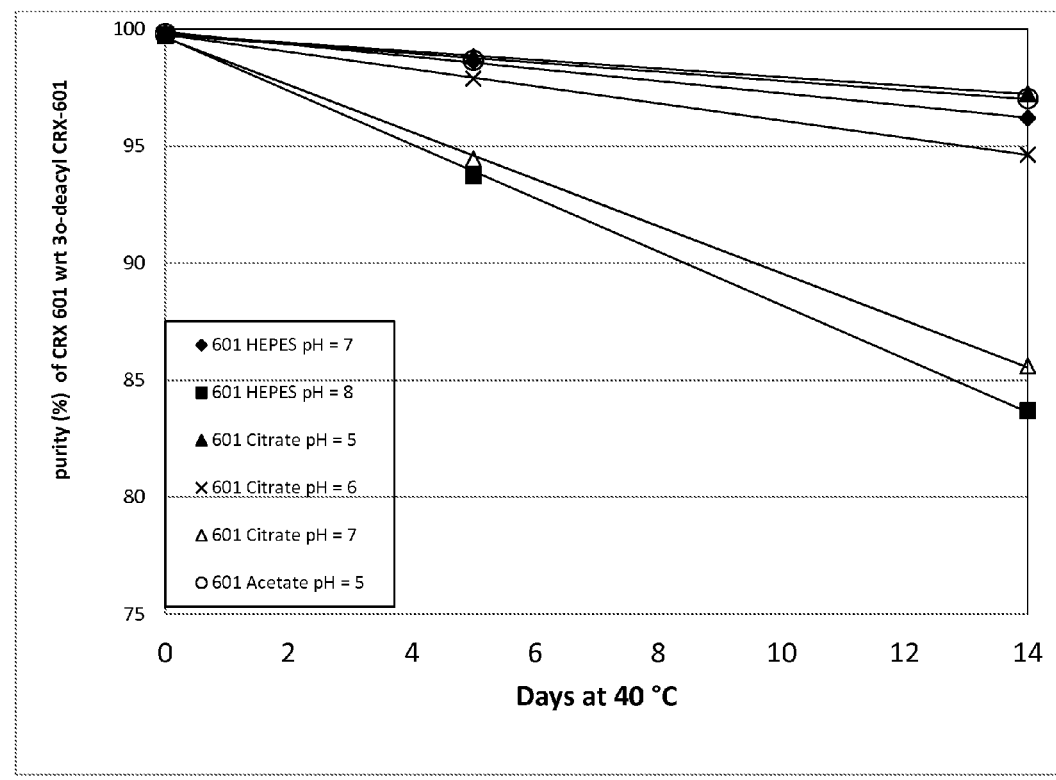
FIG. 3 shows accelerated rate of degradation for three buffers formulated with CRX-601 at a near optimal pH for each buffer.

Purity for each buffered solution was determined by measuring the percent of CRX-601 in the composition with respect to the common CRX-601 degradant. The purity data is plotted in FIG. 3 and indicates that HEPES at pH=7.0 leads to a minimum degradation, while at a different pH, (pH=5), both citrate and acetate lead to minimum degradation of CRX-601.

No significant changes in particle size were observed except for CRX-601 in citrate buffer at pH=5.0, which showed an increase in particle size. No significant change in pH was observed for any of the formulations in this study.

Example 17

Testing the Buffers with Another AGP

Figure 4:
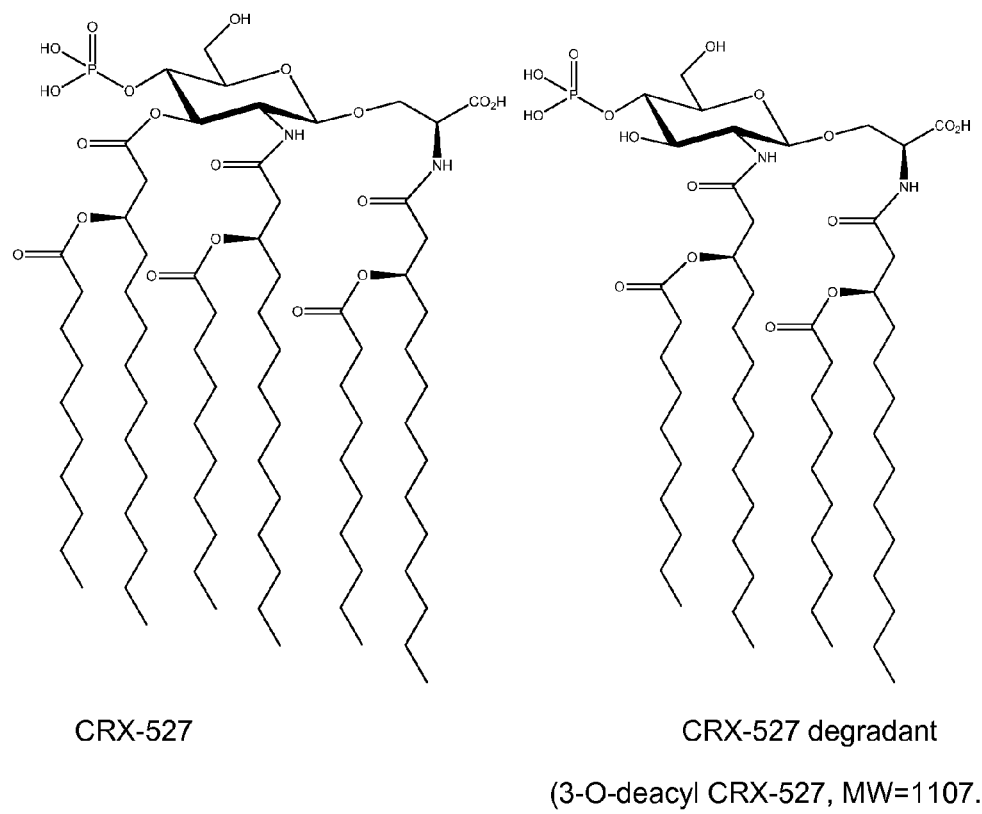
FIG. 4 shows the structure of CRX-527 and the CRX-527 degradant from the examples.
Figure 5:
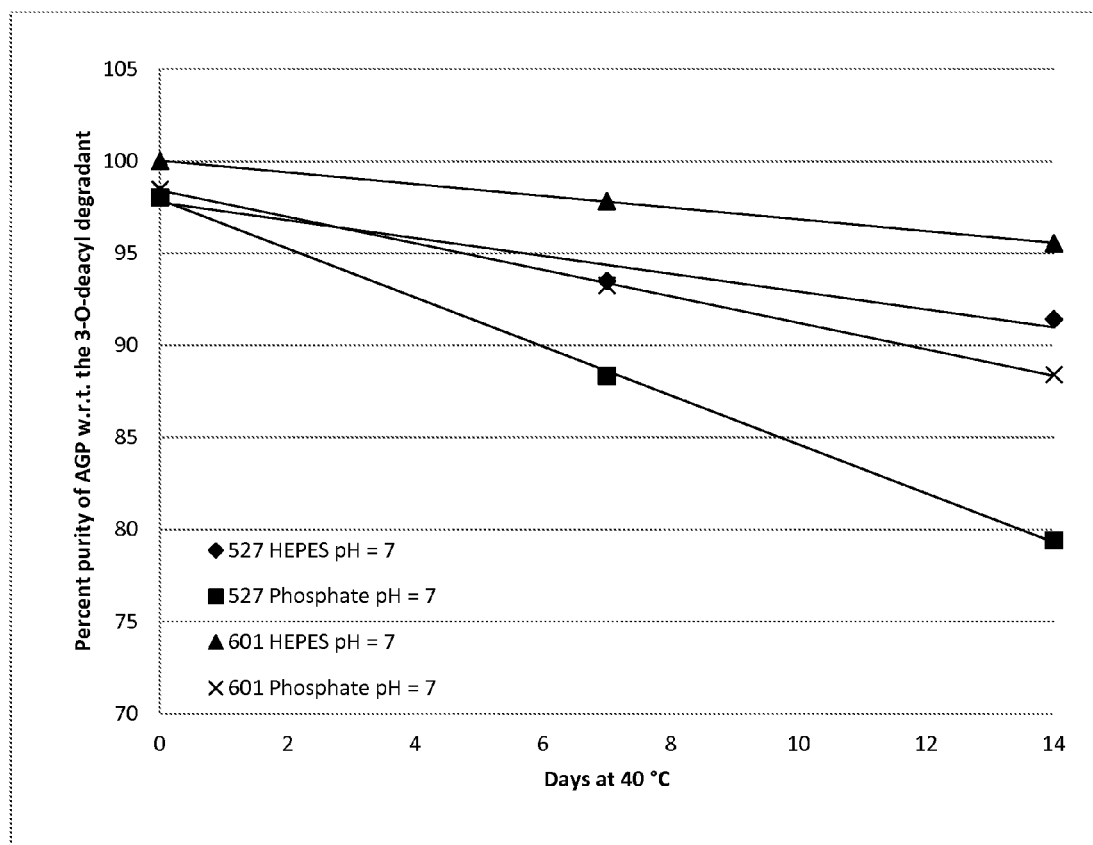
FIG. 5 shows accelerated rate of degradation using phosphate and HEPES buffers in CRX-527 and CRX-601, respectively.

Another AGP CRX-527 (obtained from GSK Vaccines, Hamilton, Mont.) was screened in the accelerated stability study for 14 days at 40° C. with the phosphate and HEPES buffer at pH=7.0. The stability of CRX-527 in each composition was determined by measuring the percent of CRX-527 in the composition with respect to common CRX-527 degradant (structures shown in FIG. 4). Likewise, purity for the buffered solution was determined by measuring the percent of CRX-601 in the composition with respect to the common CRX-601 degradant, as explained above. The plot in FIG. 5 shows the degradation profile of CRX-527 in the two buffers along with CRX-601. HEPES provided enhanced stability to the AGPs as compared against the phosphate buffer at the same pH (pH=7.0).

Example 18

CRX-601 Long Term Stability/Purity

Figure 6:
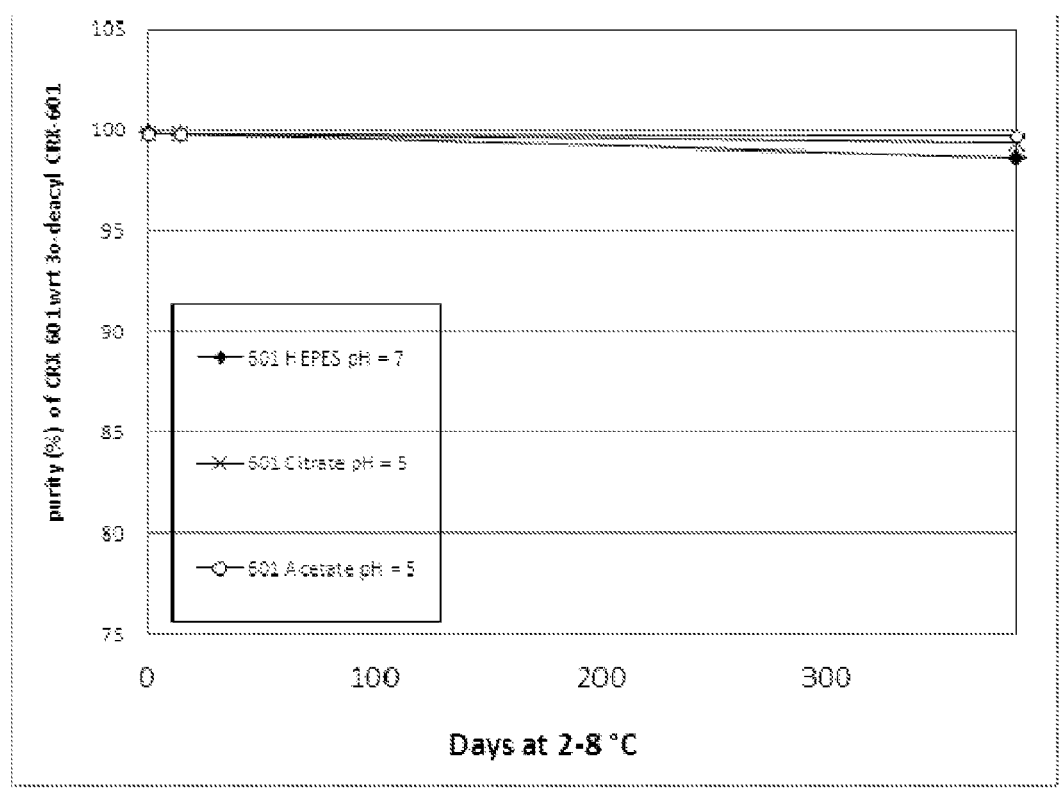
FIG. 6 shows the long term stability of CRX-601 formulated in three buffers

Buffers were evaluated to identify the effect of pH on the long term stability of CRX-601; specifically the stability of CXR-601 formulated in acetate at pH=5.0, HEPES at pH 7.0, and citrate at pH 5.0 were tested. To this end, the following buffers: HEPES at pH 7.0, citrate at pH 5.0, and acetate at pH 5.0 were prepared according to the Examples 1, 5, and 7 and CRX-601 was formulated in each of them and stored for >1 yr at 2-8° C. Purity for each buffered solution was determined by measuring the percent of CRX-601 in the composition with respect to the common CRX-601 degradant. The purity data is plotted in FIG. 6 and indicates that there is no significant degradation in any of the buffers tested over a period of ~1 yr. Thus, the HEPES buffer provides AGP compounds desired stability at notably different pH value than do the acetate and citrate buffers.

Example 19

CRX-601 Potency Testing

Figure 7:
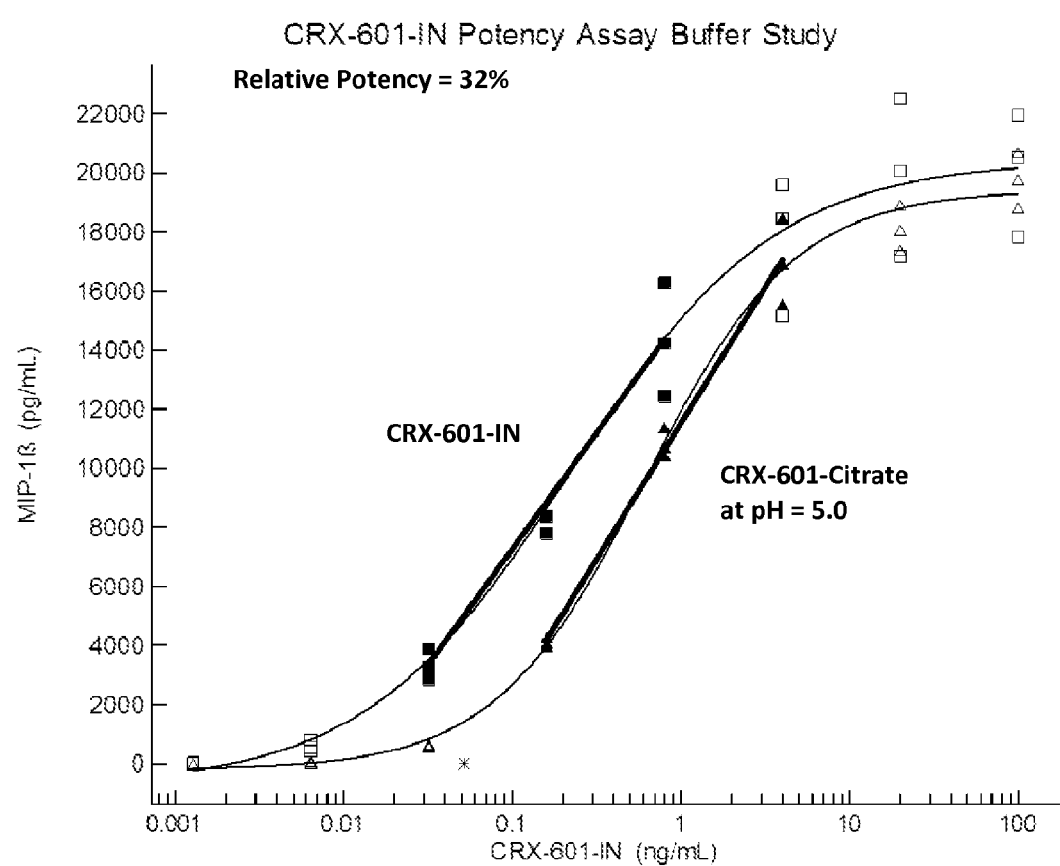
FIG. 7 through 9 show relative potency among the three buffers (HEPES, acetate, citrate) formulated with CRX-601 at a near optimal pH for each buffer.
Figure 8:
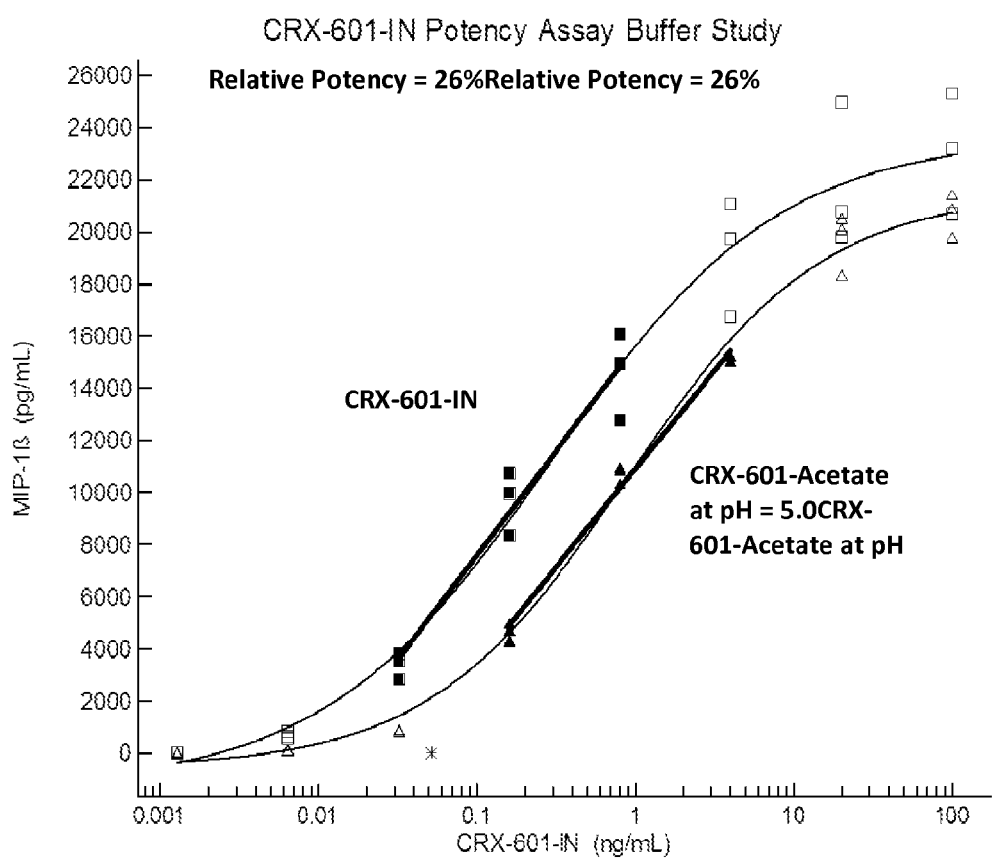
Figure 9:
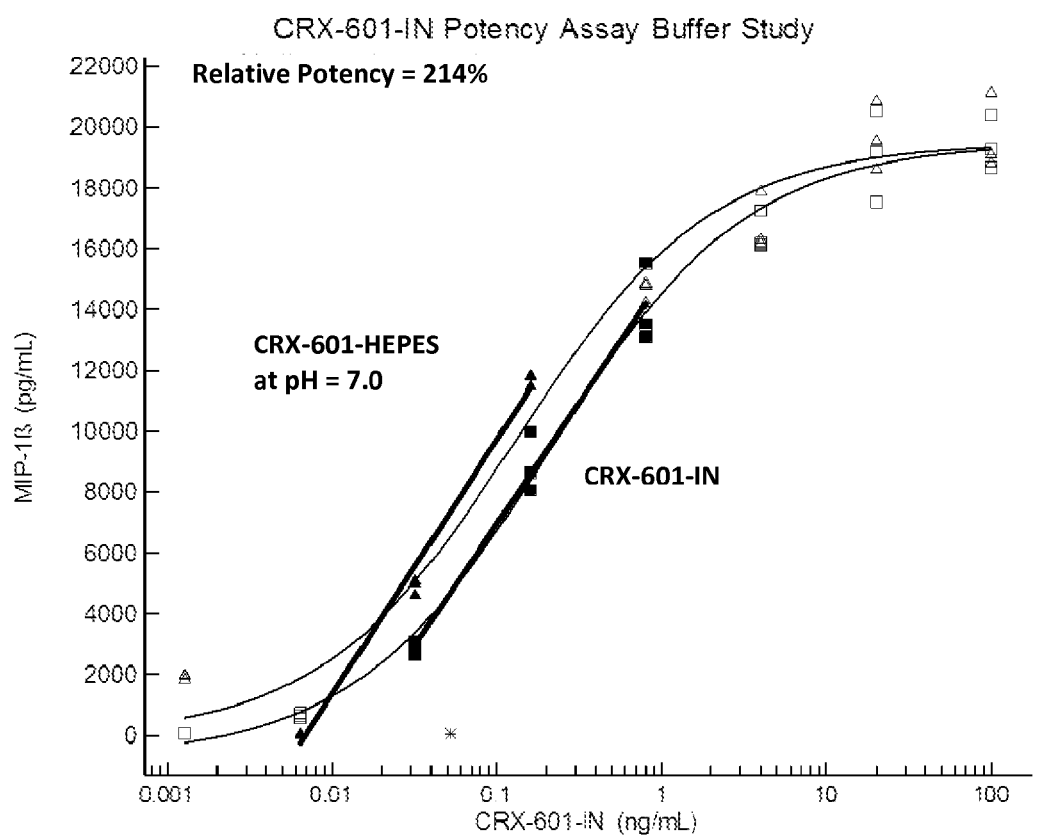

A MonoMac 6 cell potency assay was used to measure relative potency of CRX 527 in different buffers at an optimal pH and relative potency of CRX 601 in different buffers at an optimal pH. Initial experiments comparing potency of CRX-527 in HEPES and CRX-527 IN showed no significant difference in potency. (data not shown) However, notable differences in potency were observed when CRX-601 in HEPES at pH=7.0, citrate at pH=5.0, and acetate at pH=5.0 were screened in the MM6 cell potency assay against a CRX-601 IN (2% glycerol aqueous) reference formulation s. Potency results given in FIGS. 7 through 9 show that CRX-601 acetate and CRX-601 citrate had less than 50% potency compared to the CRX-601 IN. No significant cell death was observed in the acetate or the citrate buffered formulations when stained by trypan blue. In comparison, CRX-601 HEPES had a two fold increase in CRX-601 potency as compared to CRX-601 IN.

What is claimed is:

1. A composition comprising (i) an aminoalkyl glucosaminide phosphate or a pharmaceutically acceptable salt thereof and (ii) an effective amount of a HEPES buffer sufficient to provide a pharmaceutically acceptable pH range.

2. The composition of claim 1 wherein said buffer is selected from the group consisting of HEPES having a pH that is within a pharmaceutically acceptable pH range.

3. The composition according to claim 2, wherein said buffer is HEPES having a pH between about 7 and about 8.

4. The composition according to claim 2 having a pH of about 7.0.

5. The composition according to claim 2 having a pH=7.0.

6. The composition according to claim 1 wherein said aminoalkyl glucosaminide phosphate has the structure

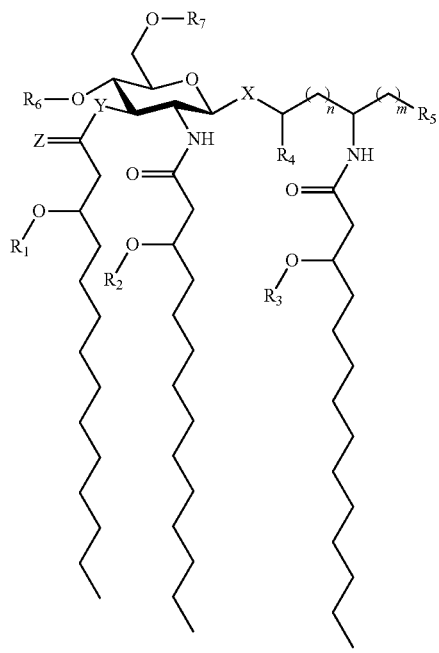

wherein m is 0 to 6 n is 0 to 4;

X is O or S;

Y is O or NH;

Z is O or H;

each $R_1$, $R_2$, $R_3$ is selected independently from the group consisting of a $C_{1-20}$ acyl and a $C_{1-20}$ alkyl;

$R_4$ is H or methyl;

$R_5$ is selected independently from the group consisting of —H, —OH, —($C_1$-$C_4$) alkoxy, —$PO_3R_8R_9$, —$OPO_3R_8R_9$, —$SO_3R_8$, —$OSO_3R_8$, —$NR_8R_9$, —SR$_8$, —CN, —NO$_2$, —CHO, —CO$_2$R$_8$, and —CONR$_8$R$_9$, wherein R$_8$ and R$_9$ are each independently selected from H and (C$_1$-C$_4$) alkyl; and each R$_6$ and R$_7$ is independently H or PO$_3$H$_2$.

7. The composition of claim 6 wherein n is an integer from 0 to 2 inclusive.

8. The composition of claim 6 wherein R$_1$, R$_2$, and R$_3$ each independently contain from about 7 to about 16 carbon atoms.

9. The composition of claim 6 wherein R$_1$, R$_2$, and R$_3$ each independently contain from about 9 to about 14 carbon atoms.

10. The composition of claim 6 wherein n is 0.

11. The composition according to claim 6 wherein R$_5$ is CO$_2$H.

12. The composition of claim 6 wherein R$_6$ is PO$_3$H$_2$.

13. The composition of claim 6 wherein R$_7$ is H.

14. The composition of claim 1 wherein said aminoalkyl glucosaminide phosphate has the structure

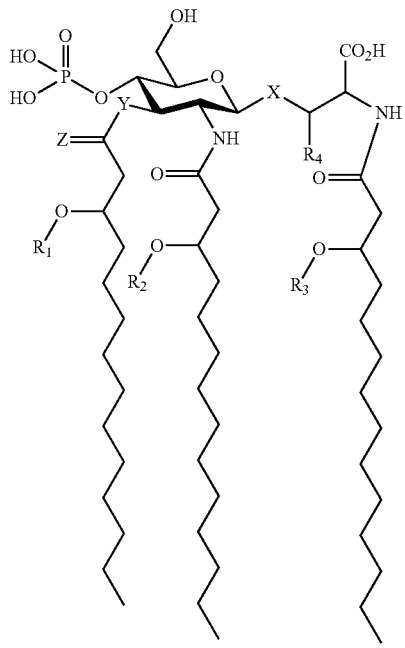

(Formula 1a)

wherein X is O or S; Y is O or NH; Z is O or H; each R$_1$, R$_2$, and R$_3$ is selected independently from the group consisting of a C1-20 acyl and a C1-20 alkyl; and R$_4$ is H or methyl.

15. The composition of claim 1 wherein said aminoalkyl glucosaminide phosphate has the structure

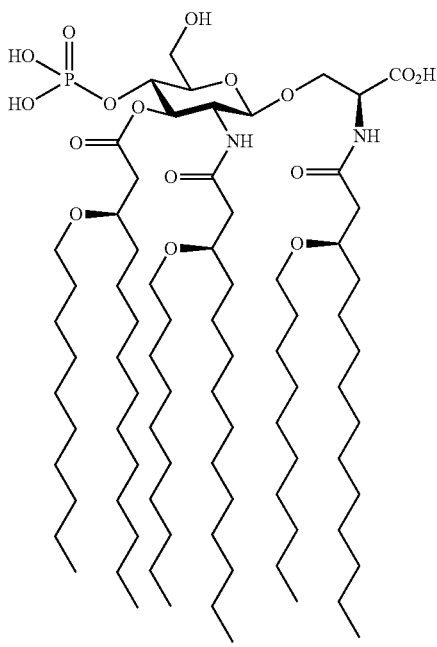

16. The composition of claim 1 wherein said aminoalkyl glucosaminide phosphate has the structure

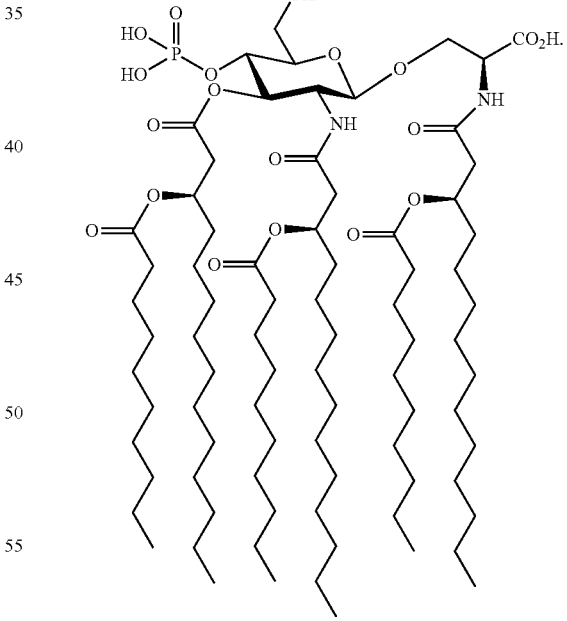

17. The composition of claim 6 wherein R$_6$ is a phosphate group and the counterion is selected from the group consisting of monoethanolamine, diethanolamine and triethanolamine.

18. The composition of claim 17 wherein the counterion is the monoethanolamine.

19. The composition of claim 14 wherein the counterion is the monoethanolamine.

20. The composition of claim 1 in the form of a dispersion.

21. The composition of claim 1 in the form of a solution.

22. The composition of claim 20 or 21 in the form of a clear solution.

23. The composition of claim 22 in which the clear solution is a nanoparticulate composition having a particle size of ≤200 nanometers.

24. The composition of claim 23 wherein said solution is used as an immunomodulator.

25. The composition of claim 1 wherein said composition has a sterile filtration particle size, as measured by dynamic light scattering (DLS) over a period of 14 days at 40 degrees Centigrade, of ≤200 nanometers.

26. The composition of claim 1 wherein said composition has a loss in percent purity after 14 days at 40 degrees Centigrade, as measured by reverse phase-high performance liquid chromatography (RP-HPLC), of 4.46% to 5.93%.

27. The composition of claim 1 wherein said composition is used as an immunomodulator.

28. The composition of claim 27 wherein said composition is used as a vaccine adjuvant.

29. The composition of claim 28 further comprising an antigen.

30. The composition according to claim 27 suitable for mucosal administration.

31. The composition according to claim 30 suitable for intranasal administration.

32. The composition of claim 27 administered to a subject in the absence of an exogenous antigen.

33. A method for enhancing an immune response of a subject comprising administering to said subject an effective amount of the composition of claim 1.

34. The method of claim 33 wherein said subject is a mammal.

35. The method of claim 34 wherein said mammal is a human.

36. The method of claim 35 further comprising administering an exogenous antigen to said subject.

37. The method of claim 36 wherein said subject is a mammal.

38. The method of claim 37 wherein said mammal is a human.

39. A method for ameliorating or substantially preventing an infectious disease, an autoimmune disease, or an allergic condition in a subject comprising administering to said subject an effective amount of the composition of claim 1.

40. The method of claim 39 wherein said subject is a mammal.

41. The method of claim 40 wherein said mammal is a human.

42. The method of claim 41 further comprising administering an exogenous antigen to said subject.

43. The method of claim 42 wherein said subject is a mammal.

44. The method of claim 43 wherein said mammal is a human.

45. A composition comprising (i) an aminoalkyl glucosaminide phosphate or a pharmaceutically acceptable salt thereof and (ii) an effective amount of a citrate or acetate buffer sufficient to provide a pharmaceutically acceptable pH.

46. The composition of claim 45 wherein the pH is not greater than 6.5.

47. The composition of claim 45 wherein the pH is between about 4.0 and about 6.0.

48. The composition of claim 47 wherein the pH is about 5.0.

* * * * *

UNITED STATES PATENT AND TRADEMARK OFFICE
CERTIFICATE OF CORRECTION

PATENT NO. : 9,827,260 B2
APPLICATION NO. : 14/777091
DATED : November 28, 2017
INVENTOR(S) : David Johnson, David Burkhart and Nupur Dutta It is certified that error appears in the above-identified patent and that said Letters Patent is hereby corrected as shown below:

In the Specification

At Column 1, Line 19 replace the paragraph under "STATEMENT REGARDING FEDERALLY SPONSORED RESEARCH" with the following paragraph:
-- This invention was made with government support under Contract # HHSN272200900008C awarded by the National Institutes of Health. The government has certain rights in the invention. --

Signed and Sealed this
Twenty-sixth Day of November, 2024

Katherine Kelly Vidal
*Director of the United States Patent and Trademark Office*